ns
| United States Patent [19] | [11] Patent Number: 4,957,681 |
| Klimesch et al. | [45] Date of Patent: Sep. 18, 1990 |

[54] PREPARATION OF PHARMACEUTICAL MIXTURES

[75] Inventors: Roger Klimesch, Alsbach-Haehnlein; Gerhard Bleckmann, Lampertheim; Lothar Schlemmer, Maxdorf, all of Fed. Rep. of Germany

[73] Assignee: BASF Aktiengesellschaft, Ludwigshafen, Fed. Rep. of Germany

[21] Appl. No.: 331,959

[22] Filed: Apr. 3, 1989

[30] Foreign Application Priority Data

Apr. 15, 1988 [DE] Fed. Rep. of Germany ....... 3812567

[51] Int. Cl.$^5$ ...................... B29C 47/00; B29C 47/60
[52] U.S. Cl. .................................. 264/211.23; 222/1; 222/77; 264/122
[58] Field of Search ............. 264/176.1, 211.23, 328.1, 264/122; 222/1, 77

[56] References Cited

U.S. PATENT DOCUMENTS

| 4,309,213 | 1/1982 | Graber et al. .......................... 71/120 |
| 4,320,041 | 3/1982 | Abe et al. ................... 264/211.23 X |
| 4,353,482 | 10/1982 | Tomlinson et al. ..................... 222/1 |
| 4,722,456 | 2/1988 | Laidlaw et al. .................. 222/77 X |

FOREIGN PATENT DOCUMENTS

| 240906 | 10/1987 | European Pat. Off. . |
| 3612211 | 10/1987 | Fed. Rep. of Germany . |
| 3612212 | 10/1987 | Fed. Rep. of Germany . |

*Primary Examiner*—Jeffery Thurlow
*Assistant Examiner*—Leo B. Tentoni
*Attorney, Agent, or Firm*—Oblon, Spivak, McClelland, Maier & Neustadt

[57] ABSTRACT

Pharmaceutical mixtures are prepared by continuous metering of the components and shaping by a conventional method.

3 Claims, No Drawings

PREPARATION OF PHARMACEUTICAL MIXTURES

BACKGROUND OF THE INVENTION

1. Field of Use

The present invention relates to a process for the preparation of pharmaceutical mixtures by continuous weighing of the individual components.

2. Description of the Background

In the pharmaceutical industry, the individual components have to date been weighed batchwise and mixed. Because of the danger of separation in the case of different bulk weights and/or flow properties, the mixed batched must be kept relatively small and transfer operations and long transport distances must be avoided. This process is inconvenient and uneconomical and furthermore does not suit modern, continuous tableting processes which do not employ granulation (which to date has always been carried out batchwise). Examples of such processes are the direct tableting of mixtures of active compound and auxiliaries and the extrusion of pharmaceutical mixtures, for example according to German Applications P 3612212.2 and 3612211.4.

The pharmaceutical industry is prejudiced against continuous metering of components for the preparation of a mixture. In the past, this prejudice was justified since the necessary metering accuracy ($\pm 5\%$ of the required value) could only be achieved over relatively long periods (several minutes) but not within short periods (less than 1 minute). To be able to use the conventional tableting machines to produce tablets whose uniformity of composition conforms to the specifications of the pharmacopeias very constant metering of each individual component to the second is necessary.

SUMMARY OF THE INVENTION

According to the present invention a continuous process is provided for the preparation of a pharmaceutical mixture having at least two components, wherein the components of the mixture are continuously weighed on electronic differential metering balances having screw conveyors at a rate of at least 50 grams per hour, which entails:

(a) continuously metering the components of the pharmaceutical mixture, thereby obtaining a substantially uniformly metered mixture, and (b) shaping the mixture.

DETAILED DESCRIPTION OF THE PREFERRED EMBODIMENTS

Through the further development of the metering balances with the use of modern electronics (latest microprocessor technology), the constancy of metering over a period of time has been decisively improved. It has now been found that they are now also suitable for use in the pharmaceutical industry. This applies in particular to their use in modern, continuous tableting processes, such as the abovementioned extrusion process. In the extruder or even in the screw zone of an injection molding machine, there is a further improvement in mixing, so that any short-term fluctuations in the composition of the mixture are compensated. Hence, these tableting processes are particularly preferred in conjunction with the novel metering process.

We have found, surprisingly, that the novel continuous metering is not only feasible, despite the prejudice which exists in the pharmaceutical industry, but in many cases even leads to more uniform metering than that achieved by the conventional batchwise process, because in the former process, in contrast to the latter, all possibility of separation is ruled out since continuous metering takes place directly at the tableting site.

In addition to this decisive advantage, the novel process has considerable advantages with regard to the requirement of space, time and personnel and is thus significantly more economical.

Although continuous metering of components has long been customary in the plastics industry, it was not obvious that it should be extended to the pharmaceutical industry since there is normally no contact between the two industries, and the pharmaceutical industry, because of its high requirements with respect to metering accuracy, believes that such processes are unsuitable for its purposes.

For the Examples, one electronic differential metering balance having screw conveyors comprising intermeshing, self-purging twin screws as a conveying element from K-TRON Soder AG, Niederlenz, CH-5702, was used per component. The individual components were metered with the aid of these balances directly into the hopper of an extruder, generally of type ZSK 30 from Werner & Pfleiderer, Stuttgart-Feuerbach, or of an injection molding machine. The throughput of total mixture was always from 2 to 5 kg/hour. To check the uniformity of the composition of the tablets, three tablets in each case were analyzed to determine their component of active compound and auxiliaries. No analyis was carried out for the content of the polymer, since this content is obtained by calculation.

In the Examples, parts and percentages are by weight.

[EXAMPLE 1]

45 parts of a copolymer having a K value (according to H. Fikentscher, Cellulose-Chemie 13 (1932), 58–64 and 71–74) of 30 and obtained from 60% of N-vinylpyrrolid-2-one (NVP) and 40% of vinyl acetate (Vac), 5 parts of stearyl alcohol and 50 parts of theophylline were metered via three of the abovementioned metering balances into the hopper of an extruder of the abovementioned type and were extruded. The temperatures of the extruder cylinder consisting of six shots were 30°, 60°, 60°, 60°, 60° and 60° C.; the die was heated to 100° C. The extrudate obtained in this procedure was pressed directly into oblong tablets using the apparatus described in claims 5 and 6 of EP-A-240 906 and the associated drawing. The analysis of these tablets gave the following result:

Active compound: 49.9, 50.2, 49.7%.

Stearyl alcohol: 5.10, 4.92, 5.03%.

[EXAMPLE 2]

50 parts of the copolymer of Example 1 and 50 parts of theophylline were mixed and extruded in a twin-screw extruder, as described in Example 1, and then pressed into oblong tablets as described in the same Example. The temperatures of the extruder shots were set at 30°, 60°, 60°, 60°, 90° and 120° C. The die was likewise at 120° C.

Analysis of active compound content: 49.3, 50.1 and 50.5%.

[EXAMPLE 3]

47.5 parts of a copolymer having a K value of 30 and obtained from 60% of NVP and 40% of Vac, 2.5 parts of crosslinked polyvinylpyrrolidone (PVP) as a tablet disintegrant and 50 parts of theophylline were mixed and extruded in a twin-screw extruder, as described in Example 1, and then molded as described there. The five shots were each at 120° C. and the die was at 130° C.

Analysis of active compound content: 50.6, 50.1 and 49.8%.

[EXAMPLE 4]

50 parts of the copolymer having a K value of 52 and obtained from 30% of NVP and 70% of Vac and 50 parts of theophylline werre mixed and extruded in a twin-screw extruder, as described in Example 1, and were pressed to give tablets. The temperatures of the five shots were 30°, 60°, 100°, 100° and 120° C. The die was likewise heated to 120° C.

Analysis of active compound content: 50.8, 49.9 and 49.6%.

[EXAMPLES 5 TO 8]

A mixture of 50% of an NVP homopolymer having the K value stated in each case in the Table and 50% of theophylline was metered, as described in Example 1, into a single-screw extruder, melted at the temperature stated in each case in the Table, extruded, and pressed to give tablets as described in Example 1. Thereafter, the active compound content of three tablets in each case was determined.

| Example | K value | 1. | 2. | T [°C.] 3. | 4. | 5. Shot | Die | Theophylline content (%) | | |
|---|---|---|---|---|---|---|---|---|---|---|
| 5 | 12 | 115 | 125 | 135 | 135 | 135 | 145 | 51.0 | 49.4 | 49.6 |
| 6 | 17 | 125 | 125 | 135 | 45 | 145 | 155 | 49.9 | 50.8 | 49.2 |
| 7 | 25 | 145 | 155 | 165 | 175 | 175 | 175 | 50.3 | 49.1 | 50.7 |
| 8 | 30 | 150 | 160 | 160 | 170 | 180 | 180 | 49.1 | 50.5 | 50.8 |

[EXAMPLE 9]

40 parts of a copolymer of 60% of NVP and 40% of Vac, having a K value of 30, 10 parts of polyhydroxyethyl methacrylate and 50 parts of theophylline were processed as described in Example 1. Temperatures of the shots: 70°, 80°, 80°, 80°, 80° C. Die: 90° C. Active compound content: 50.2, 50.4 and 49.8%.

[EXAMPLE 10]

50 parts of a commercial, 80% hydrolyzed polyvinyl acetate and 50 parts of theophylline were processed similarly to Example 1. The temperatures of the shots were 100°, 100°, 110°, 120° and 130° C. Die: 150° C. Theophylline content: 49.1, 50.9 and 49.8%.

EXAMPLE 11

50 parts of polyhydroxyethyl methacrylate having a K value of 30 and 50 parts of theophylline were processed as described in Example 1. Temperatures of the shots: 120°, 130°, 150°, 160°, 160° C. Die: 170° C. Theophylline content: 49.8, 50.4 and 50.1%.

EXAMPLES 12 TO 14

36 parts of a copolymer of 60% of NVP and 40% of Vac, having a K value of 30, 4 parts of stearyl alcohol, 40 parts of theophylline and 20 parts of starch in Example (12), lactose in Example (13) and sucrose in Example (14) were metered into a 6-shot twin-screw extruder as described in Example 1, extruded, and pressed to give tablets as described there. The temperatures of the shots were 90°, 100°, 110°, 120°, 120° and 130° C. and the temperature of the die was 135° C. The theophylline content was 50.0, 50.3 and 50.1% in Example (12), 50.4, 49.9 and 49.6% in Example (13) and 49.9, 50.3 and 49.7% in Example (14).

EXAMPLES 15 TO 17

50 parts of the copolymer of Examples 12 to 14 and 50 parts of verapamil were converted into tablets as described in Examples 12 to 14. The verapamil content was 49.8, 49.6 and 50.0% in Example (15), 50.1, 49.8 and 50.4% in Example (16) and 50.3, 50.5 and 49.9% in Example (17).

The Examples below were carried out similarly to the above Examples. The processing conditions and the contents of active compound and monomeric auxiliary found are shown in the Table.

TABLE

| Example No. | Active compound | Polymer | Auxiliary | Weight ratio of active compound/polymer/auxiliary | T1 | T2 | T3 | T4 | T5 | T6 | Die | Active compound content (%) | | | Auxiliary content (%) | | |
|---|---|---|---|---|---|---|---|---|---|---|---|---|---|---|---|---|---|
| 18 | Pseudoephedrine 47.5 Diphenhydramine 2.5 | A | ./. | 50/50/0 | 60 | 80 | 100 | 120 | 120 | 120 | 120 | 47.6 2.55 | 47.1 2.48 | 47.8 2.53 | | | |
| 19 | Propafenone | A | Starch | 40/40/20 | | | | | | | | | | | | | |
| 20 | Propafenone | A | StA | 60/35/5 | 80 | 90 | 100 | 120 | 110 | 110 | 110 | 40.1 | 39.6 | 40.0 | 5.05 | 5.02 | 4.97 |
| 21 | Propafenone | A | StA | 60/30/10 | 80 | 90 | 100 | 120 | 140 | 140 | 140 | 59.6 | 59.9 | 60.4 | 9.92 | 10.08 | 10.10 |
| 22 | Propafenone | A | StS | 60/35/5 | 70 | 90 | 100 | 110 | 130 | 130 | 140 | 60.3 | 60.1 | 59.5 | 4.93 | 4.99 | 5.00 |
| 23 | Propafenone | A | StA | 50/40/10 | 65 | 80 | 95 | 110 | 115 | 115 | 115 | 60.5 | 59.8 | 60.6 | 10.10 | 10.09 | 10.01 |
| 24 | Propafenone | B | MgSt | 60/35/5 | 60 | 70 | 80 | 80 | 95 | 100 | 110 | 50.0 | 49.4 | 50.3 | 5.05 | 4.99 | 4.98 |
| 25 | Propafenone | A | MgSt | 50/40/10 | 60 | 60 | 80 | 80 | 95 | 100 | 100 | 60.8 | 60.1 | 60.3 | 9.95 | 9.94 | 10.03 |
| 26 | Anipamil | A | MgSt | 50/40/10 | 30 | 30 | 50 | 40 | 60 | 60 | 60 | 49.8 | 50.2 | 50.5 | 10.06 | 10.00 | 9.98 |
| 27 | Vitamin B1 | B | ./. | 50/50/0 | 40 | 40 | 50 | 60 | 60 | 60 | 80 | 50.7 | 49.5 | 49.4 | | | |
| 28 | Nicotinic Acid | A | StA | 50/50/0 | 60 | 70 | 80 | 95 | 95 | 100 | 100 | 49.3 | 49.9 | 50.2 | | | |
| 29 | Biperiden | B | ./. | 50/45/5 | 80 | 90 | 100 | 120 | 120 | 130 | 135 | 50.4 | 50.2 | 50.8 | 4.96 | 4.98 | 5.05 |
| 30 | Biperiden | A | ./. | 50/50/0 | 80 | 90 | 110 | 120 | 140 | 140 | 140 | 50.2 | 50.0 | 49.6 | | | |
| 31 | Canthaxantin | B | ./. | 50/50/0 | 30 | 30 | 40 | 40 | 60 | 60 | 60 | 50.6 | 49.9 | 50.1 | | | |
| 32 | Canthaxantin | A | ./. | 50/50/0 | 40 | 40 | 55 | 60 | 60 | 80 | 80 | 50.1 | 49.7 | 50.5 | | | |
| 33 | Indomethacin | B | ./. | 25/75 | 50 | 60 | 70 | 80 | 80 | 80 | 80 | 24.8 | 24.9 | 24.8 | | | |
| 34 | Indomethacin | A | | 25/75 | 60 | 80 | 100 | 120 | 120 | 120 | 120 | 24.9 | 25.0 | 25.1 | | | |
| 35 | Anipamil | A | | 25/75 | 30 | 30 | 40 | 50 | 50 | 60 | 60 | 24.7 | 25.0 | 25.2 | | | |
| 36 | Anipamil | B | | 25/75 | 30 | 30 | 40 | 50 | 50 | 50 | 60 | 25.2 | 24.9 | 24.9 | | | |
| 37 | Benzocaine | D | | 25/75 | 60 | 80 | 95 | 100 | 120 | 120 | 140 | 24.8 | 25.3 | 25.0 | | | |
| 38 | Benzocaine | D | | 25/75 | 60 | 80 | 95 | 120 | 120 | 130 | 120 | 25.1 | 24.8 | 25.8 | | | |
| 39 | Benzocaine | F | | 25/75 | 30 | 30 | 40 | 50 | 50 | 60 | 60 | 24.9 | 25.1 | 24.9 | | | |
| 40 | Benzocaine | B | | 25/75 | 60 | 80 | 100 | 120 | 120 | 120 | 120 | 24.8 | 25.0 | 25.2 | | | |
| 41 | 5,5-Diphenhydramine | B | | 25/75 | 60 | 80 | 100 | 120 | 120 | 120 | 120 | 25.0 | 25.0 | 25.0 | | | |
| 42 | Paracetamide | B | | 25/75 | 60 | 80 | 80 | 80 | 90 | 90 | 120 | 25.1 | 25.1 | 24.8 | | | |
| 43 | Sulfathiazole | B | | 25/75 | 65 | 75 | 80 | 90 | 90 | 90 | 120 | 24.8 | 25.1 | 24.8 | | | |
| 44 | Sulfathiazole | E | | 25/75 | 70 | 80 | 100 | 100 | 100 | 100 | 120 | 25.0 | 24.7 | 25.1 | | | |
| 45 | Benzocaine | A | | 25/75 | 70 | 90 | 100 | 110 | 110 | 110 | 70 | 29.8 | 25.0 | 25.1 | | | |
| 46 | 5,5-Diphenhydramine | A | | 25/75 | 30 | 30 | 40 | 50 | 50 | 60 | 70 | 24.9 | 25.2 | 25.2 | | | |
| 47 | Paracetamol | A | | 25/75 | 60 | 80 | 100 | 120 | 120 | 120 | 130 | 25.0 | 24.8 | 24.8 | | | |
| 48 | Sulfathiazole | A | | 50/50 | 70 | 90 | 95 | 100 | 100 | 100 | 130 | 50.5 | 50.1 | 49.7 | | | |
| 49 | Vitamin C | C | | 50/50 | 75 | 95 | 95 | 120 | 120 | 120 | 120 | 49.3 | 49.8 | 50.1 | | | |
| 50 | Benzocaine | E | | 25/75 | 60 | 70 | 80 | 120 | 130 | 130 | 130 | | | | 24.9 | 24.7 | 24.9 |
| 51 | Benzocaine | G | | 25/75 | 50 | 70 | 80 | 80 | 80 | 80 | 120 | | | | 25.0 | 24.8 | 25.1 |
| 52 | Benzocaine | H | | 25/75 | 50 | 60 | 70 | 70 | 80 | 75 | 110 | | | | 25.2 | 25.2 | 25.0 |
| 53 | Benzocaine | I | | 25/75 | 50 | 60 | 70 | 80 | 80 | 80 | 80 | | | | 24.9 | 25.3 | 25.1 |
| 54 | Metoprolol | A | StA | 40/55/5 | 60 | 70 | 80 | 80 | 90 | 80 | 80 | 39.7 | 39.8 | 40.1 | 4.99 | 5.00 | 5.08 |
| 55 | Ranitidine | A | — | 46/54 | 65 | 70 | 80 | 80 | 90 | 90 | 90 | 46.2 | 46.5 | 46.0 | | | |
| 56 | Diclophenac | A | StA | 40/55/5 | 65 | 75 | 80 | 90 | 90 | 90 | 90 | 40.2 | 40.4 | 40.2 | 4.93 | 4.95 | 5.01 |
| 57 | Furosemide | A | StA | 30/60/10 | 60 | 70 | 80 | 90 | 90 | 100 | 100 | 29.7 | 30.1 | 30.2 | 10.0 | 10.1 | 10.1 |
| 58 | Nifedipine | A | StA | 20/70/10 | 50 | 60 | 60 | 80 | 80 | 80 | 80 | 20.0 | 20.0 | 19.9 | 9.9 | 10.1 | 10.1 |
| 59 | Gallopamil | A | StA | 40/54/6 | 50 | 60 | 70 | 80 | 80 | 70 | 70 | 39.9 | 40.4 | 39.7 | 5.93 | 6.04 | 6.05 |
| 60 | Gallopamil | A | StA | 40/48/12 | 50 | 60 | 70 | 80 | 80 | 70 | 70 | 40.1 | 39.7 | 40.4 | 12.1 | 12.1 | 12.0 |
| 61 | Gallopamil | A | StA | 40/42/18 | 50 | 60 | 70 | 80 | 80 | 70 | 70 | 39.7 | 40.0 | 39.9 | 17.8 | 18.1 | 18.7 |
| 62 | Gallopamil | A | StS | 40/54/6 | 50 | 60 | 70 | 80 | 80 | 70 | 70 | 40.3 | 40.1 | 39.8 | 5.93 | 5.93 | 6.09 |
| 63 | Gallopamil | A | StS | 40/48/12 | 50 | 60 | 70 | 80 | 80 | 70 | 70 | 39.8 | 40.3 | 40.4 | 12.0 | 12.0 | 11.9 |
| 64 | Gallopamil | A | StS | 40/42/18 | 50 | 60 | 70 | 80 | 80 | 70 | 70 | 40.4 | 39.9 | 39.7 | 17.9 | 17.8 | 18.0 |
| 65 | Anipamil | A | StA | 34/54.4/13.6 | 45 | 55 | 60 | 65 | 60 | 60 | 55 | 34.4 | 34.3 | 33.8 | 13.5 | 13.7 | 13.6 |
| 66 | Biperiden | A | StA | 6/89/5 | | | 60 | 65 | 65 | 65 | 60 | 5.99 | 6.07 | 6.09 | 5.06 | 5.07 | 5.00 |

TABLE-continued

| Example No. | Active compound | Polymer | Auxiliary | Weight ratio of active compound/ polymer/auxiliary | T1 | T2 | T3 | T4 | T5 | T6 | Die | Active compound content (%) | | | Auxiliary content (%) | | |
|---|---|---|---|---|---|---|---|---|---|---|---|---|---|---|---|---|---|
| 67 | Biperiden | A | StA | 6/84/10 | 45 | 55 | 50 | 65 | 65 | 65 | 60 | 5.92 | 6.05 | 6.06 | 9.9 | 9.9 | 10.0 |
| 68 | Biperiden | A | StA | 6/79/15 | 45 | 55 | 60 | 65 | 65 | 65 | 60 | 6.06 | 6.01 | 5.92 | 14.9 | 14.9 | 15.2 |
| 69 | Biperiden | A | StA | 6/74/20 | 50 | 50 | 55 | 60 | 60 | 50 | 50 | 5.98 | 5.98 | 5.99 | 19.8 | 20.0 | 19.9 |
| 70 | Biperiden | A | StA | 6/69/25 | 40 | 50 | 55 | 60 | 60 | 50 | 50 | 5.93 | 5.98 | 5.99 | 25.1 | 25.2 | 25.0 |
| 71 | Biperiden | A | StA | 6/64/30 | 40 | 50 | 55 | 60 | 60 | 50 | 50 | 5.94 | 6.07 | 5.97 | 30.1 | 30.3 | 29.7 |
| 72 | Biperiden | A | StA | 6/59/35 | 40 | 50 | 55 | 60 | 60 | 50 | 50 | 5.94 | 6.09 | 6.07 | 34.9 | 35.6 | 34.8 |
| 73 | Bezafibrate | A | — | 61.5/38.5 | 60 | 70 | 80 | 80 | 80 | 80 | 80 | 62.0 | 61.8 | 61.2 | | | |
| 74 | Bezafibrate | A | StA | 61.5/34/4.5 | 60 | 70 | 50 | 50 | 50 | 70 | 70 | 62.1 | 61.9 | 60.9 | 4.45 | 4.47 | 4.55 |
| 75 | Bezafibrate | A | StA | 61.5/29.5/9.0 | 40 | 45 | 80 | 80 | 80 | 80 | 50 | 61.4 | 60.9 | 61.9 | 8.93 | 9.04 | 8.98 |
| 76 | Metoprolol | A | Starch | 40/45/15 | 60 | 70 | 80 | 70 | 70 | 80 | 80 | 40.4 | 39.8 | 40.0 | | | |
| 77 | Metoprolol | A | Starch | 40/35/25 | 55 | 60 | 65 | 80 | 70 | 70 | 70 | 40.2 | 40.1 | 39.7 | | | |
| 78 | Anipamil | A | Lactose | 32/43/25 | 55 | 60 | 70 | 80 | 70 | 65 | 65 | 31.8 | 32.0 | 32.2 | | | |
| 79 | Anipamil | A | Cellulose | 32/61.2/6.8 | 55 | 60 | 70 | 80 | 65 | 65 | 60 | 32.0 | 31.9 | 32.2 | | | |
| 80 | Anipamil | A | Lactose | 32/34.4/13.6 | 55 | 60 | 70 | 80 | 65 | 65 | 60 | 32.3 | 32.2 | 31.8 | | | |
| 81 | Anipamil | A | Starch | 32/54.4/13.6 | 55 | 60 | 70 | 80 | 65 | 65 | 60 | 32.0 | 31.8 | 32.0 | | | |
| 82 | Caffeine powder | A | StA | 50/45/5 | 65 | 75 | 90 | 90 | 90 | 90 | 100 | 50.4 | 50.2 | 50.3 | 5.06 | 4.97 | 4.95 |
| 83 | Caffeine powder | A | — | 50/50 | 65 | 75 | 90 | 90 | 90 | 90 | 100 | 50.2 | 50.3 | 49.8 | | | |
| 84 | Caffeine granules | A | StA | 50/45/5 | 65 | 70 | 70 | 75 | 75 | 90 | 80 | 50.0 | 49.5 | 49.6 | 4.95 | 4.98 | 5.03 |
| 85 | Caffeine granules | A | — | 50/50 | 65 | 70 | 70 | 75 | 75 | 90 | 80 | 50.2 | 50.5 | 49.8 | | | |

A = Copolymer of 60% by weight of NVP and 40% by weight of vinyl acetate, K value about 33
B = PVP, K value 12
C = PVP, K value 17
D = Mowiol ® 30-92 (92% hydrolyzed polyvinyl alcohol)
E = Mowiol 4-80 (80% hydrolyzed polyvinyl alcohol)
F = Copolymer of NVP, vinyl acetate and hydroxypropyl acrylate in a weight ratio of 30:40:30; K value about 18
G = Cellulose acetate
H = Cellulose acetate phthalate
I = Vinyl acetate/crotonic acid copolymer; K value about 40
StA = Stearyl alcohol
StS = Stearic acid
MgSt = Magnesium stearate

EXAMPLE 86

50 parts of a copolymer having a K value of 30 and obtained from 60% of NVP and 40% of Vac and 50 parts of theophylline were metered continuously into the hopper of an injection molding machine and processed to give 1 cm long oblong tablets at 120° C. Active compound content: 50.8, 49.4 and 50.5%.

EXAMPLE 87

47.5 parts of the copolymer of Example 86, 2.5 parts of stearyl alcohol and 50 parts of theophylline were metered continuously into an injection molding machine and processed to give tablet cores at 100° C. The mold was left at room temperature. Theophylline content: 49.9, 50.3 and 50.9%. Content of stearyl alcohol: 2.56, 2.49 and 2.44%.

EXAMPLE 88

25% of paracetamol and 75% of PVP having a K value of 12, which had been prepared according to DE-A-36 42 633 in water using an organic peroxide as an initiator, were metered continuously into the feed orifices of an injection molding machine and converted into tablet cores at a die temperature of 130° C. Active compound content: 24.7, 25.2 and 24.9%.

EXAMPLES 89 AND 90

Example 88 was repeated using phenytoin and benzocaine as the active compound. Contents of active compound: 25.1, 25.3 and 24.9% of phenytoin in Example (89) and 24.8, 25.2 and 24.5% of benzocaine in Example (90).

We claim:

1. A continuous process for the preparation of a pharmaceutical mixture having at least two components, wherein the components of the mixture are continuously metered which comprises:
   (a) continuously metering the individual components of the pharmaceutical mixture at a rate of at least 50 g/h on electronic differential metering balances having a metering accuracy of at least ±5% within time intervals less than 1 minute and having screw conveyors, thereby obtaining a substantially uniformly metered mixture, and
   (b) shaping said mixture.

2. The continuous process as claimed in claim 1, wherein said electronic differential metering balances having screw conveyors comprise intermeshing, self-purging twin screws as a conveying element.

3. The continuous process as claimed in claim 1, wherein said mixture containing said metered components is shaped into tablets.

* * * * *